United States Patent

Winter et al.

Patent Number: 5,328,969
Date of Patent: Jul. 12, 1994

[54] PROCESS FOR THE PREPARATION OF A HIGH MOLECULAR WEIGHT OLEFIN POLYMER

[75] Inventors: Andreas Winter, Glashütten/Taunus; Jürgen Rohrmann; Volker Dolle, both of Kelkheim; Frank Küber, Oberursel, all of Fed. Rep. of Germany

[73] Assignee: Hoechst Aktiengesellschaft, Frankfurt, Fed. Rep. of Germany

[21] Appl. No.: 980,643

[22] Filed: Nov. 24, 1992

[30] Foreign Application Priority Data

Nov. 30, 1991 [DE] Fed. Rep. of Germany ....... 4139596

[51] Int. Cl.$^5$ ................................................ C08F 4/64
[52] U.S. Cl. ..................... 526/127; 526/160; 526/170; 502/155
[58] Field of Search ................ 526/160, 170, 127

[56] References Cited

U.S. PATENT DOCUMENTS 5,017,714  5/1991  Welborn, Jr. ............... 526/160
5,132,262  7/1992  Rieger et al. ............... 526/160

FOREIGN PATENT DOCUMENTS 0363029  4/1990  European Pat. Off.
4035886  of 0000  Fed. Rep. of Germany
4128238  of 0000  Fed. Rep. of Germany
3826075  2/1990  Fed. Rep. of Germany

OTHER PUBLICATIONS

Ewen, J. A., et al, *J. Am. Chem. Soc.* 109:6544–6545 (1987).

Primary Examiner—Joseph L. Schofer
Assistant Examiner—David Wu
Attorney, Agent, or Firm—Connolly and Hutz

[57] ABSTRACT

A very active catalyst system for olefin polymerization comprises a cocatalyst, preferably an aluminoxane, and a metallocene of the formula I

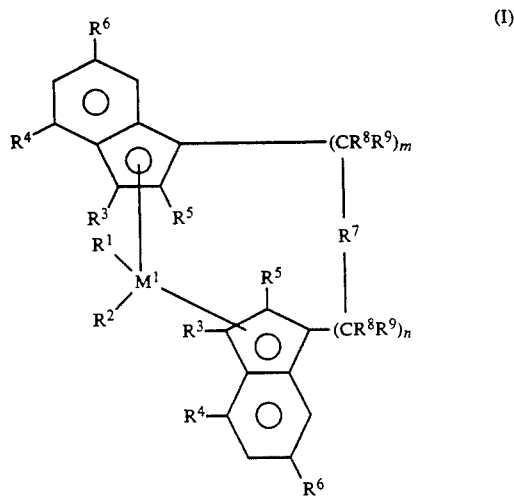

in which, preferably, $M^1$ is Zr or Hf, $R^1$ and $R^2$ are alkyl or halogen, $R^3$ is hydrogen, $R^4$ to $R^6$ are alkyl or aryl, $-(CR^8R^9)_m-R^7-(CR^8R^9)_n$ is a single- or multi-membered chain, in which $R^7$ can also be a (substituted) hetero atom, and $m+n$ is zero or 1.

7 Claims, No Drawings

PROCESS FOR THE PREPARATION OF A HIGH MOLECULAR WEIGHT OLEFIN POLYMER

The invention relates to a process for the preparation of olefin polymers of high isotacticity, narrow molecular weight distribution and high molecular weight.

Polyolefins of high molecular weight are of particular importance for the production of films, sheets or large hollow articles, such as, for example, pipes or moldings.

The preparation of polyolefins using soluble metallocene compounds in combination with aluminoxanes or other cocatalysts which, on the basis of their Lewis acidity, can convert the neutral metallocene into a cation and can stabilize it is known from the literature.

For example, a specific preactivation method for the metallocene using an aluminoxane, which leads to a considerable increase in the activity of the catalyst system and to a significant improvement in the particle morphology of the polymer, has been proposed (cf. DE 37 26 067). Although the preactivation increases the molecular weight, no substantial increase can be achieved.

It has been possible to realize a further but still inadequate increase in the molecular weight by using metallocenes of high metallocene activity which are specifically bridged with hetero atoms (EP-A 0 336 128).

Catalysts based on ethylenebisindenylhafnium dichloride and ethylene-bis(4,5,6,7-tetrahydro-1-indenyl)hafnium dichloride and methylaluminoxane, with which higher molecular weight polypropylenes can be prepared by suspension polymerization, furthermore are known (cf. J. A. Ewen et al., J. Am. Chem. Soc. 109 (1987) 6544). Under industrially relevant polymerization conditions, however, the particle morphology of polymers produced in this way is unsatisfactory and the activity of the catalysts employed is comparatively low. Associated with the high catalyst costs, inexpensive polymerization is thus not possible using these systems.

It has been possible to achieve a significant increase in the molecular weight by using metallocenes in which the aromatic π-ligands fixed by a bridge carry substituents in the 2-position (DE-P 40 35 886.0) or in the 2- and 4-position (DE-P 41 28 238.8).

Under the constraint of inexpensive production on a large industrial scale, the polymerization must be carried out at the highest possible reaction temperatures, since at higher polymerization temperatures, the heat of polymerization formed can be removed with less cooling medium, and the polymerization can therefore be realized with significantly smaller dimensions of the cooling water circulation.

The metallocenes last mentioned with substituents in the 2- or 2- and 4-position relative to the bridge are already very efficient in this respect at a polymerization temperature of 70° C., but the molecular weights which can be achieved at industrially relevant polymerization temperatures (for example 70° C.) are still too low for some industrial uses, such as, for example, preparation of polymers for pipes and large hollow articles, as well as specific fibers.

There was the object of discovering a process or a catalyst system which produces polymers of good particle morphology and high molecular weight in a high yield. The entire molecular weight range can be covered by only one metallocene by using hydrogen as the molecular weight regulator.

It has been found that this object can be achieved by using bridged metallocene systems substituted in a certain manner in the ligand sphere.

The invention thus relates to a process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$ with the atoms joining them, can form a ring, at a temperature of from −60° to 200° C., under a pressure of 0.5 to 100 bar, in solution, in suspension or in the gas phase, in the presence of a catalyst which is formed from a metallocene as the transition metal compound and a cocatalyst, which comprises using as the metallocene a compound of the formula I

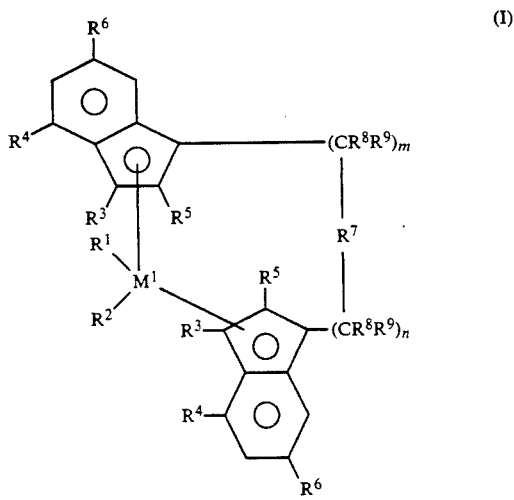

in which $M^1$ is a metal of group IVb, Vb or VIb of the periodic table, $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom, the radicals $R^3$ are identical or different and are a hydrogen atom, a halogen atom, a $C_1$–$C_{10}$-alkyl group, which can be halogenated, a $C_6$–$C_{10}$-aryl group, which can be halogenated, or a —$NR_2^{10}$, —$SR^{10}$, —$OSiR_3^{10}$, —$SiR_3^{10}$ or —$PR_2^{10}$ radical, in which $R^{10}$ is a halogen atom, a $C_1$–$C_{10}$-alkyl group or a $C_6$–$C_{10}$-aryl group, $R^4$ to $R^6$ are identical or different and have the meaning given for $R^3$, with the proviso that $R^4$ and $R^6$ are not hydrogen, $R^7$ is

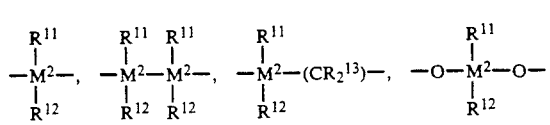

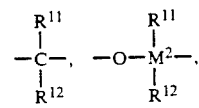

=BR$^{11}$, =AlR$^{11}$, —Ge—, —Sn—, —O—, —S—, =SO, =SO$_2$, =NR$^{11}$, =CO, =PR$^{11}$ or =P(O)R$^{11}$ in which R$^{11}$, R$^{12}$ and R$^{13}$ are identical or different and are a hydrogen atom, a halogen atom, a C$_1$-C$_{10}$-alkyl group, a C$_1$-C$_{10}$-fluoroalkyl group, a C$_6$-C$_{10}$-aryl group, a C$_6$-C$_{10}$-fluoroaryl group, a C$_1$-C$_{10}$-alkoxy group, a C$_2$-C$_{10}$-alkenyl group, a C$_7$-C$_{40}$-arylalkyl group, a C$_8$-C$_{40}$-arylalkenyl group or a C$_7$-C$_{40}$-alkylaryl group, or R$^{11}$ and R$^{12}$, or R$^{11}$ and R$^{13}$, in each case with the atoms joining them, form a ring, M$^2$ is silicon, germanium or tin, R$^8$ and R$^9$ are identical or different and have the meaning given for R$^{11}$ and m and n are identical or different and are zero, 1 or 2, m plus n being zero, 1 or 2.

Alkyl is straight-chain or branched alkyl. Halogen (halogenated) is fluorine, chlorine, bromine or iodine, preferably fluorine or chlorine.

In spite of having the same designation, the substituents R$^4$-R$^6$ on the two indenyl radicals can be different (cf. definition of R$^3$).

The present invention furthermore relates to the polyolefins prepared by the process described.

The catalyst to be used for the process according to the invention comprises a cocatalyst and a metallocene of the formula I.

In formula I, M$^1$ is a metal of group IVb, Vb or VIb of the periodic table, for example titanium, zirconium, hafnium, vanadium, niobium, tantalum, chromium, molybdenum or tungsten, preferably zirconium, hafnium and titanium.

R$^1$ and R$^2$ are identical or different and are a hydrogen atom, a C$_1$-C$_{10}$-, preferably C$_1$-C$_3$-alkyl group, a C$_1$-C$_{10}$-, preferably C$_1$-C$_3$-alkoxy group, a C$_6$-C$_{10}$-, preferably C$_6$-C$_8$-aryl group, a C$_6$-C$_{10}$-, preferably C$_6$-C$_8$-aryloxy group, a C$_2$-C$_{10}$-, preferably C$_2$-C$_4$-alkenyl group, a C$_7$-C$_{40}$-, preferably C$_7$-C$_{10}$-arylalkyl group, a C$_7$-C$_{40}$-, preferably C$_7$-C$_{12}$-alkylaryl group, a C$_8$-C$_{40}$-, preferably C$_8$-C$_{12}$-arylalkenyl group or a halogen atom, preferably chlorine.

The radicals R$^3$ are identical or different and are a hydrogen atom, a halogen atom, preferably a fluorine, chlorine or bromine atom, a C$_1$-C$_{10}$-, preferably C$_1$-C$_4$-alkyl group, which can be halogenated, a C$_6$-C$_{10}$-, preferably C$_6$-C$_9$-aryl group, which can be halogenated, or a -NR$_2^{10}$, -SR$^{10}$, -OSiR$_3^{10}$, -SiR$_3^{10}$ or -PR$_2^{10}$ radical, in which R$^{10}$ is a halogen atom, preferably a chlorine atom, or a C$_1$-C$_{10}$-, preferably C$_1$-C$_3$-alkyl group or C$_6$-C$_{10}$-, preferably C$_6$-C$_8$-aryl group. R$^3$ particularly preferably is hydrogen, C$_1$-C$_4$-alkyl or C$_6$-C$_9$-aryl.

R$^4$ to R$^6$ are identical or different and have the meaning described for R$^3$, with the proviso that R$^4$ and R$^6$ may not be hydrogen. Preferably, R$^4$ to R$^6$ are (C$_1$-C$_4$)-alkyl or C$_6$-C$_9$-aryl, both of which can be halogenated, such as methyl, ethyl, propyl, isopropyl, butyl, isobutyl, trifluoromethyl, phenyl, tolyl or mesityl, in particular methyl, isopropyl or phenyl.

R$^7$ is

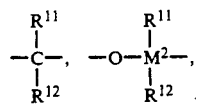

=BR$^{11}$, =AlR$^{11}$, —Ge—, —Sn—, —O—, —S—, =SO, =SO$_2$, =NR$^{11}$, =CO, =PR$^{11}$ or =P(O)R$^{11}$ in which R$^{11}$, R$^{12}$ and R$^{13}$ are identical or different and are a hydrogen atom, a halogen atom, a C$_1$-C$_{10}$-, preferably C$_1$-C$_4$-alkyl group, in particular the methyl group, a C$_1$-C$_{10}$-fluoroalkyl group, preferably the CF$_3$ group, a C$_6$-C$_{10}$-, preferably C$_6$-C$_8$-aryl group, a C$_6$-C$_{10}$-fluoroaryl group, preferably the pentafluorophenyl group, a C$_1$-C$_{10}$-, preferably C$_1$-C$_4$-alkoxy group, in particular the methoxy group, a C$_2$-C$_{10}$-, preferably C$_2$-C$_4$-alkenyl group, a C$_7$-C$_{40}$-, preferably C$_7$-C$_{10}$-arylalkyl group, a C$_8$-C$_{40}$-, preferably C$_8$-C$_{12}$-arylalkenyl group or a C$_7$-C$_{40}$-, preferably C$_7$-C$_{12}$-alkylaryl group, or R$^{11}$ and R$^{12}$, or R$^{11}$ and R$^{13}$, in, each case together with the atoms joining them, form a ring.

M$^2$ is silicon, germanium or tin, preferably silicon and germanium.

R$^7$ is preferably =CR$^{11}$R$^{12}$, =SiR$^{11}$R$^{12}$, =GeR$^{11}$R$^{12}$, —O—, —S—, =SO, =PR$^{11}$ or =P(O)R$^{11}$.

R$^8$ and R$^9$ are identical or different and have the meaning given for R$^{11}$.

m and n are identical or different and are zero, 1 or 2, preferably zero or 1, m plus n being zero, 1 or 2, preferably zero or 1.

The particularly preferred metallocenes are thus the compounds of the formulae A, B and C

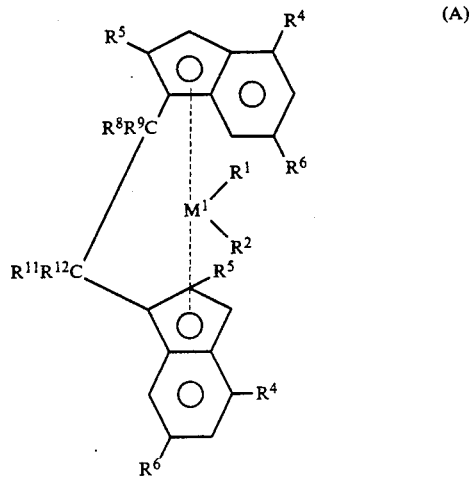

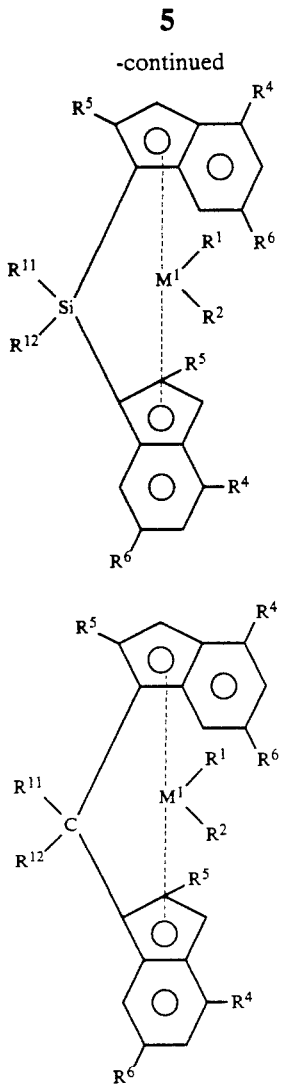

The metallocenes described above can be prepared in accordance with the following equation:

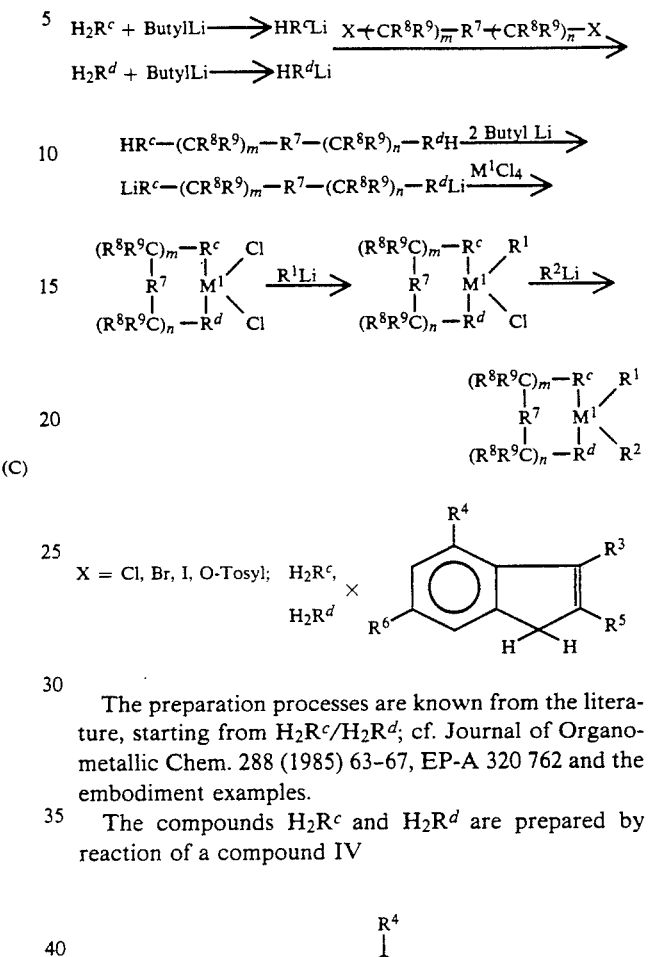

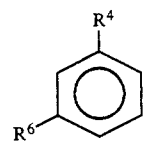

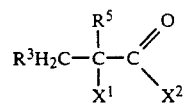

The preparation processes are known from the literature, starting from $H_2R^c/H_2R^d$; cf. Journal of Organometallic Chem. 288 (1985) 63-67, EP-A 320 762 and the embodiment examples.

The compounds $H_2R^c$ and $H_2R^d$ are prepared by reaction of a compound IV

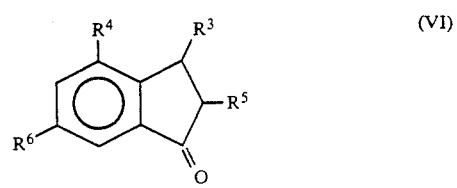

where
- $M^1$ = Zr or Hf; $R^1$ $R^2$ = methyl or chlorine; $R^4$ and $R^6$ = methyl, isopropyl, phenyl, ethyl or trifluoromethyl; $R^5$ = hydrogen and the meanings given for $R^4$ and $R^6$, and $R^8$, $R^9$, $R^{11}$ and $R^{12}$ have the above-mentioned meanings, in particular the compounds I mentioned in the embodiment examples.

Preferably, $R^5$ is other than hydrogen and has the meanings of $R^4$ and $R^6$.

This means that the indenyl radicals of the compounds I are substituted in particular in the 2,4,6-position ($R^3$ = H).

The chiral metallocenes are preferably employed as the racemate. However, the pure R- or S-form can also be used. Optically active polymer can be prepared with these pure stereoisomeric forms. However, the meso form of the metallocenes should be removed, since the polymerization-active center (the metal atom) in these compounds is no longer chiral, because of mirror symmetry on the central metal, and no highly isotactic polymer can therefore be produced. If the meso form is not removed, atactic polymer is also formed, alongside isotactic polymer. This may be entirely desirable for certain uses—flexible shaped articles, for example.

The separation of the stereoisomers is known in principle.

with a compound V $$R^3H_2C-\overset{R^5}{\underset{X^1}{C}}-\overset{O}{\underset{X^2}{C}}$$

or an anhydride thereof, in the presence of a Friedel-Crafts catalyst. In this formula, $X^1$ and $X^2$ are a nucleophilic leaving group, such as, for example, halogen, the hydroxyl group or a tosyl group; in particular bromine or chlorine.

The indanones VI or VIa are obtained (VI)

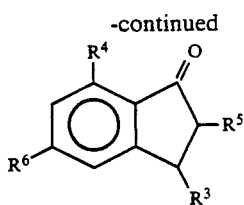

The indanones can be obtained in the form of two structural isomers of the formula VI or VIa, depending on the substitution pattern on the aromatic radical. These isomers can be reduced, in the pure form or as a mixture, by methods known from the literature using reducing agents such as NaBH$_4$ or LiAlH$_4$ to give the corresponding indanols, and these can then be dehydrated with acids, such as sulfuric acid, oxalic acid or p-toluenesulfonic acid, or by treatment with dehydrating substances, such as magnesium sulfate, sodium sulfate, aluminum oxide, silica gel or molecular sieves, to give indenes of the formula VII or VIIa (H$_2$R$^c$/H$_2$R$^d$) (Bull. Soc. Chim. Fr. 11 (1973) 3092; Organomet. 9 (1990) 3098 and the embodiment examples).

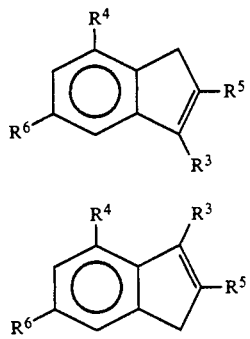

Suitable Friedel-Crafts catalysts are, for example, AlCl$_3$, AlBr$_3$, FeCl$_3$, SbCl$_5$, SnCl$_4$, BF$_3$,TiCl$_4$, ZnCl$_2$, HF, H$_2$SO$_4$, polyphosphoric acid, H$_3$PO$_4$ or an AlCl$_3$-/NaCl melt; in particular AlCl$_3$.

The starting compounds of the formulae IV and V are known and are commercially obtainable, or they can be prepared by processes which are known from the literature.

The reaction is carried out in an inert solvent. Methylene chloride or CS$_2$ is preferably employed. If the starting components are liquid, a solvent can also be dispensed with.

The molar ratios of the starting compounds, including the Friedel-Crafts catalyst, can vary within wide limits. The molar ratio of compound I:II: catalyst is preferably 1:0.5–1.5:1–5; in particular 1:1:2.5–3.

The reaction temperature is preferably 0° C. to 130° C., in particular 25° C. to 80° C.

The reaction times as a rule vary between 30 minutes and 100 hours, preferably between 2 hours and 30 hours.

Preferably, a mixture of the compounds IV and V is initially introduced into the reaction vessel and the Friedel-Crafts catalyst is metered in. The reverse sequence of addition is also possible.

The indanones of the formula VI or VIa can be purified by distillation, column chromatography or crystallization.

The substituted indenes can be obtained as double bond isomers (VII/VIIa). These can be purified from by-products by distillation, column chromatography or crystallization.

Starting from the indenes of the formulae VII and VIIa, which can be employed as an isomer mixture, the preparation of the metallocenes I proceeds by processes which are known from the literature (cf. AU-A-31478/89, J. Organomet. Chem. 342 (1988) 21, EP-A 284 707 and the embodiment examples) in accordance with the equation described.

According to the invention, an aluminoxane of the formula (II)

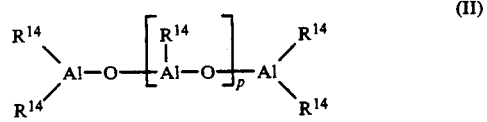

for the linear type, and/or of the formula (III)

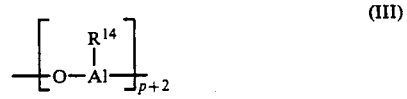

for the cyclic type, in which, in the formulae (II) and (III), the radicals R$^{14}$ can be identical or different and are a C$_1$-C$_6$-alkyl group, a C$_6$-C$_{18}$-aryl group, benzyl or hydrogen and p is an integer from 2 to 50, preferably 10 to 35, is preferably used as the cocatalyst.

Preferably, the radicals R$^{14}$ are identical and are methyl, isobutyl, phenyl or benzyl, particularly preferably methyl.

If the radicals R$^{14}$ are different, they are preferably methyl and hydrogen, or alternatively methyl and isobutyl, hydrogen and isobutyl preferably being present to the extent of 0.01–40% (number of radicals R$^{14}$).

The aluminoxane can be prepared in various ways by known processes. One of the methods is, for example, to react an aluminum-hydrocarbon compound and/or a hydridoaluminum-hydrocarbon compound with water (gaseous, solid, liquid or bonded—for example as water of crystallization) in an inert solvent (such as, for example, toluene). To prepare an aluminoxane having different alkyl groups R$^{14}$, two different aluminum trialkyls (AlR$_3$+AlR'$_3$), corresponding to the desired composition, are reacted with water (cf. S. Pasynkiewicz, Polyhedron 9 (1990) 429 and EP-A 302 424).

The precise structure of the aluminoxanes II and III is not known.

Regardless of the nature of the preparation, all aluminoxane solutions have the common feature of a varying content of unreacted aluminum starting compound, which is present in the free form or as an adduct.

It is possible for the metallocene to be preactivated with an aluminoxane of the formula (II) and/or (III) before use in the polymerization reaction. In this way, the polymerization activity is increased significantly and the particle morphology is improved.

The preactivation of the transition metal compound is carried out in solution. Preferably, in this procedure, the metallocene is dissolved in a solution of the aluminoxane in an inert hydrocarbon. An aliphatic or aromatic hydrocarbon is a suitable inert hydrocarbon. Toluene is preferably used.

The concentration of the aluminoxane in the solution is in the range from about 1% by weight up to the saturation limit, preferably 5 to 30% by weight, in each case based on the total solution. The metallocene can be employed in the same concentration, but it is preferably employed in an amount of $10^{-4}-1$ mol per mol of aluminoxane. The preactivation time is 5 minutes to 60 hours, preferably 5 to 60 minutes. The preactivation is carried out at a temperature of from $-78°$ C. to $100°$ C., preferably $0°$ to $70°$ C.

The metallocene can also be prepolymerized or applied to a support. The (or one of the) olefin(s) employed in the polymerization is (are) preferably used for the prepolymerization.

Suitable supports are, for example, silica gels, aluminum oxides, solid aluminoxane or other inorganic support materials. A polyolefin powder in finely divided form is also a suitable support material.

According to the invention, compounds of the formulae $R_xNH_{4-x}BR'_4$, $R_xPH_{4-x}BR'_4$, $R_3CBR'_4$ or $BR'_3$ can be used as suitable cocatalysts instead of or alongside an aluminoxane. In these formulae, x is a number from 1 to 4, preferably 3, the radicals R are identical or different, preferably identical, and are $C_1-C_{10}$-alkyl or $C_6-C_{18}$-aryl, or 2 radicals R, together with the atom joining them, form a ring, and the radicals R' are identical or different, preferably identical, and are $C_6-C_{18}$-aryl, which can be substituted by alkyl, haloalkyl or fluorine.

In particular, R is ethyl, propyl, butyl or phenyl and R' is phenyl, pentafluorophenyl, 3,5-bistrifluoromethylphenyl, mesityl, xylyl or tolyl (cf. EP-A 277 003, EP-A 277 004 and EP-A 426 638).

If the abovementioned cocatalysts are used, the actual (active) polymerization catalyst comprises the reaction product of the metallocene and one of the compounds mentioned. This reaction product is therefore preferably first prepared in a separate step outside the polymerization reactor, using a suitable solvent.

In principle, any compound which, on the basis of its Lewis acidity, can convert the neutral metallocene into a cation and can stabilize this ("labile coordination") is suitable according to the invention as the cocatalyst. Moreover, the cocatalyst or the anion formed from it should not undergo other reactions with the metallocene cation formed (cf. EP-A 427 697).

To remove catalyst poisons present in the olefin, purification with an aluminum alkyl, for example $AlMe_3$ or $AlEt_3$, is advantageous. This purification either can be carried out in the polymerization system itself, or the olefin is brought into contact with the Al compound before addition into the polymerization system, and is then separated off again.

The polymerization or copolymerization is carried out in a known manner in solution, in suspension or in the gas phase, continuously or discontinuously, in one or more stages at a temperature of from $-60°$ to $200°$ C., preferably $30°$ to $80°$ C., particularly preferably $50°$ to $80°$ C. Olefins of the formula $R^a$—CH=CH—$R^b$ are polymerized or copolymerized. In this formula, $R^a$ and $R^b$ are identical or different and are a hydrogen atom or an alkyl radical having 1 to 14 carbon atoms However, $R^a$ and $R^b$ with the carbon atoms joining them, can also form a ring. Examples of such olefins are ethylene, propylene, 1-butene, 1-hexene, 4-methyl-l-pentene, 1-octene, norbornene or norbornadiene. In particular, propylene and ethylene are polymerized.

If necessary, hydrogen is added as a molecular weight regulator and/or to increase the activity. The overall pressure in the polymerization system is 0.5 to 100 bar. Polymerization in the pressure range of 5 to 64 bar, which is of particular industrial interest, is preferred.

The metallocene is used here in a concentration, based on the transition metal, of $10^{-3}$ to $10^{-8}$, preferably $10^{-4}$ to $10^{-7}$ mol of transition metal per $dm^3$ of solvent or per $dm^3$ of reactor volume. The aluminoxane is used in a concentration of $10^{-5}$ to $10^{-1}$ mol, preferably $10^{-4}$ to $10^{-2}$ mol per $dm^3$ of solvent or per $dm^3$ of reactor volume. The other cocatalysts mentioned are used in approximately equimolar amounts to the metallocene. In principle, however, higher concentrations are also possible.

If the polymerization is carried out as suspension or solution polymerization, an inert solvent customary for the Ziegler low pressure process is used. For example, the polymerization is carried out in an aliphatic or cycloaliphatic hydrocarbon; examples of these which may be mentioned are propane, butane, pentane, hexane, heptane, isooctane, cyclohexane and methylcyclohexane.

A gasoline or hydrogenated diesel oil fraction furthermore can be used. Toluene can also be used. The polymerization is preferably carried out in the liquid monomer.

If inert solvents are used, the monomers are metered into the reaction vessel in gaseous or liquid form.

The polymerization can be of any desired length, since the catalyst system to be used according to the invention shows only a slight decrease in polymerization activity with respect to time.

The process according to the invention is distinguished by the fact that, in the temperature range of between $50°$ and $80°$ C., which is of particular industrial interest, the metallocenes described produced polymers of high molecular weight, high stereospecificity and good particle morphology.

In particular, the zirconocenes according to the invention advance into a molecular weight range, or even exceed this, which was reserved for the hafnocenes in the previous prior art. However, these hafnocenes had the disadvantage of only a low polymerization activity and very high catalyst costs, and the polymers prepared with them had a poor powder morphology.

The following examples are intended to illustrate the invention in more detail.

The abbreviations have the following meanings:

| | | |
|---|---|---|
| VN = | viscosity number in $cm^3/g$ | |
| $M_w$ = | weight-average molecular weight in g/mol | determined by gel permeation chromatography |
| $M_w/M_n$ = | polydispersity | |
| m.p. = | melting point, determined by differential scanning calorimetry ($20°$ C./minute heating up/— cooling down rate) | |
| II = | isotactic index (II = mm + ½ mr), determined by $^{13}$C-NMR spectroscopy | |
| MFI/(230/5) = | melt flow index, measured in accordance with DIN 53735; in dg/min | |
| BD = | polymer bulk density in $g/dm^3$ | |

SYNTHESIS OF THE METALLOCENES USED IN THE EXAMPLES

Example A 2,5,7-Trimethyl-1-indanone ( 1 )

107 g (810 mmol) of AlCl$_3$ were slowly added to a solution of 34.4 g (324 mmol) of m-xylene (99% pure) and 74 g (324 mmol) of 2-bromoisobutyryl bromide (98% pure) in 600 ml of analytical grade methylene chloride via a solids metering funnel at room temperature, while stirring vigorously, whereupon vigorous evolution of gases started. The mixture was stirred at room temperature for 15 hours, poured onto ice-water, which was acidified with 25 ml of concentrated HCl, and extracted several times with ether. The combined organic phases were washed first with a saturated NaHCO$_3$ solution and then with a saturated NaCl solution, and dried with magnesium sulfate. The oil which remained after the solvent had been stripped off under reduced pressure was distilled over a short distillation bridge. 52.4 g of the indanone 1 passed over at 81°–90° C./0.1–0.2 mbar in the form of a colorless oil, which crystallized at room temperature. The yield was 93%.

$^1$H-NMR spectrum (100 MHz, CDCl$_3$): 7.05 (1,s), 6.87 (1,s), 3.25 (1,q), 2.43–2.80 (2,m), 2.57 (3,s), 2.35 (3,s), 1.25 (3,d).

Mass spectrum: 174 M$^+$, correct disintegration pattern.

Example B 2,4,6-Trimethylindene (2)

20.4 g (117 mmol) of 2,5,7-trimethyl-1-indanone (1) were dissolved in 300 ml of a mixture of tetrahydrofuran/-methanol (2:1), and 6.6 g (175 mmol) of NaBH$_4$ were added at room temperature. The mixture was stirred for a further hour, 50 ml of half-concentrated HCl were added and the mixture was extracted with ether. The combined organic phases were dried over sodium sulfate and freed from the solvent. The residue was transferred to a distillation apparatus, and 13 g of magnesium sulfate were added. A vacuum of about 10 mbar was applied and the mixture was heated up until the product distilled over (130°–150° C.). The distillation gave 17.7 g of the indene 2 as a colorless oil. The yield was 96%.

Mass spectrum: 158 M$^+$, correct disintegration pattern.

Example C

2-Methyl-5,7-diisopropyl-1-indanone (3) and 2-Methyl-4,6-diisopropyl-1-indanone (3a)

174 g (1300mmol) of AlCl$_3$ were slowly added to a solution of 84.8 g (523 mmol) of 1,3-diisopropylbenzene and 120 g (523 mmol) of 2-bromoisobutyryl bromide (98% pure) in 600 ml of analytical grade methylene chloride via a solids metering funnel at room temperature. The mixture was heated under reflux for a further 20 hours and then worked up analogously to Example A. The crude product was chromatographed on 3 kg of silica gel 60. The indanones 3 and 3a were able to be eluted separately with a mobile phase mixture of hexane/15% ethyl acetate. The compound 2-methyl-5-isopropyl-1-indanone followed as a by-product in a further zone with the same mobile phase. However, separation of the two isomers is not necessary for the further reactions. The overall yield was 93 g (78%). $^1$H-NMR spectrum (360 MHz, CDCl$_3$): isomer mixture (3:2) 7.49 (d), 7.36 (d), 7.13 (s), 7.10 (s), 4.15 (septet), 3.25–3.40 (m), 3.10 (septet), 2.90–3.00 (m), 2.60–2.73 (m), 1.22–1.30 (m).

Mass spectrum: 230 M$^+$, correct disintegration pattern.

Example D

2-Methyl-4,6-diisopropylindene (4) and 2-methyl-5,7-diisopropylidene (4a), variant I 19.3 g (511 mmol) of NaBH$_4$ were added to a solution of 78.5 g (341mmol) of the isomer mixture 3/3a in 700 ml of a solvent mixture of tetrahydrofuran/analytical grade methanol (2:1) at room temperature. After the mixture had been stirred at room temperature for 2 hours, 120–130 ml of half-concentrated HCl were added, and the mixture was extracted with ether. The combined organic phases were dried with Na$_2$SO$_4$. The residue which remained after the solvent had been stripped off was taken up in 500 ml of methylene chloride, and the mixture was heated under reflux with 6.5 g (34mmol) of p-toluenesulfonic acid for 15 minutes. The residue which remained after the solvent had been stripped off was chromatographed on 1.5 kg of silica gel 60.56 g of the isomer mixture 4/4a were able to be isolated in the form of a colorless oil with a mobile phase mixture of hexane/diisopropyl ether 20:1. The overall yield was 86%.

$^1$H-NMR spectrum (100 MHz, CDCl$_3$): double bond isomers (1:1) 7.1 (m), 6.95 (m), 6.60 (m), 6.43 (m), 3.25 (br), 2.75–3.20 (m), 2.12 (d), 1.28 (d), 1.25 (d).

Mass spectrum: 214 M$^+$, correct disintegration pattern.

Example E

2-Methyl-4,6-diisopropylindene (4) and 2-methyl-5,7-diisopropylindene (4a), variant II 19.3 g (511 mmol) of NaBH$_4$ were added to a solution of 78.5 g (341mmol) of the isomer mixture 3/3a in 700 ml of a solvent mixture of tetrahydrofuran/analytical grade methanol (2:1) at room temperature. After the mixture had been stirred at room temperature for 2 hours, 120–130 ml of half-concentrated HCl were added and the mixture was extracted with ether. The combined organic phases were dried with Na$_2$SO$_4$. The residue which remained after the solvent had been stripped off was transferred to a distillation apparatus, and 50 mg of magnesium sulfate were added. After a vacuum of about 1 mbar had been applied, the mixture was heated up until the product passed over (about 130° C.). 65 g of the isomer mixture 4/4a were obtained as a colorless oil. The yield was 90%.

Example F

Dimethylbis ( 2-methyl-4,6-diisopropylindenyl ) silane ( 5 )

9.2 ml (22.8 mmol) of a 2.5M butyllithium solution in hexane were added to a solution of 4.9 g (22.8 mmol) of the isomer mixture 4/4a in 25 ml of tetrahydrofuran at 0° C. under Ar as an inert gas, and the mixture was heated under reflux for a further hour. The red solution was then added dropwise to a solution of 1.5 g (11.4 ml) of dimethyldichlorosilane in 10 ml of tetrahydrofuran at room temperature, and the mixture was heated under reflux for 8 hours. The batch was poured onto ice-water and extracted with ether. The ether phase was dried over magnesium sulfate and evaporated under reduced pressure. The yellowish oil which remained was then chromatographed on 500 g of silica gel 60. 1.4 g of the indene mixture 4/4a were able to be eluted first with a mobile phase mixture of hexane/5% methylene chloride. The ligand system 11 followed with hexane/8% methylene chloride. The viscous oil which remained after the mobile phase had been stripped off was able to be crystallized by stirring with methanol in an ice-bath. 3.1 g of a yellowish solid were obtained. The yield was 56%, or 84% with respect to the indene reacted.

$^1$H-NMR spectrum (100 MHz, CDCl$_3$): double bond isomers (3:1) 6.82–7.32 (m), 6.70 (m), 6.62 (m), 6.52 (m), 3.75 (s,br), 3.65 (s,br), 3.35 (s), 2.70–3.30 (m), 2.05–2.25 (m), 1.10–1.45 (m), 0.10–0.22 (m), −0.15 to −0.32 (m).

Mass spectrum: 484 M$^+$, correct disintegration.

Example G

Dimethylsilanediylbis ( 2-methyl-4,6-diisopropylindenyl )-zirconium chloride ( 6 )

6.3 ml (16.2 mmol) of a 2.5M butyllithium solution in hexane were added to a solution of 3.1 g (6.5 mmol) of the ligand system 5 in 25 ml of diethyl ether at room temperature under Ar as an inert gas, and the mixture was stirred overnight. After addition of 10 ml of hexane, the beige-colored suspension was filtered and the residue was washed with 20 ml of hexane. The dilithium salt was dried under an oil pump vacuum for a long time and then added to a suspension of 1.6 g (6.8 mmol) of ZrCl$_4$ in 30 ml of methylene chloride at −78° C. The mixture was warmed to room temperature in the course of 1 hour, and stirred at this temperature for a further 30 minutes. After the solvent had been stripped off, the orange-brown residue was extracted with 50 ml of hexane. After the solvent had been stripped off, 2.6 g (60%) of the complex 6 were obtained in the form of a yellow powder. The ratio of the racemate to the meso form was 3:1. 1.3 g (30%) of the complex 6 were able to be obtained as the pure racemate (yellow crystalline powder) by recrystallization from hexane.

$^1$H-NMR spectrum (100 MHz, CDCl$_3$): 7.27 (2,s,aromatic-H), 7.05 (2,s,aromatic-H), 6.80 (2,s,β-Ind—H), 2.6–3.2 (4,m,i—Pr—CH), 2.22 (6,s,Ind—CH$_3$), 1.15–1.40 (30,m,i—Pr—CH$_3$,Si—CH$_3$). Mass spectrum: 642M$^+$ (with respect to $^{90}$Zr), correct isotope pattern, correct disintegration.

Example H

Dimethylbis ( 2,4,6-trimethylindenyl ) silane ( 7 )

25.5 ml (63.7 mmol) of a 2.5 M butyllithium solution in hexane were added to a solution of 10.1 g (64 mmol) of the indene 2 in 50 ml of tetrahydrofuran at room temperature under Ar as an inert gas, and the mixture was heated under reflux for 1 hour. The solution thus obtained was added dropwise to a solution of 4.1 g (32 mmol) of dimethyldichlorosilane in 20 ml of tetrahydrofuran at room temperature, and the mixture was heated under reflux for 3 hours. The reaction mixture was poured onto ice-water and extracted several times with ether. The combined organic phases were dried over sodium sulfate and evaporated under reduced pressure. The residue was chromatographed on 450 g of silica gel 60. 2.5 g of the indene 2 were able to be eluted first with a mobile phase mixture of hexane/5% methylene chloride. 6.5 g of the ligand system 7 (isomers) followed with hexane/8% methylene chloride. The yield was 54%, or 72% with respect to the indene 2 reacted.

Example J

Dimethylsilanediylbis ( 2,4,6-trimethylindenyl ) zirconium dichloride ( 8 )

6.6 ml (16.2 mmol) of a 2.5M butyllithium solution in hexane were added to a solution of 2.0 g (5.4 mmol) of the ligand system 7 in 30 ml of diethyl ether at room temperature under Ar as an inert gas, and the mixture was stirred at this temperature for 5–6 hours. The solution was evaporated completely. The solid residue which remained was washed in portions with a total of 30 ml of hexane and dried under an oil pump vacuum for a long time. The beige-colored powder thus obtained was added to a suspension of 1.23 g (5.5 mmol) of zirconium tetrachloride in 30 ml of methylene chloride at −78° C. After the reaction mixture had been warmed to room temperature, it was evaporated completely and the residue was dried under an oil pump vacuum. The solid residue comprised a mixture of the racemic form with the meso form in a ratio of 1:1. This residue was first washed with a small amount of hexane. It was then extracted with a total of 120 ml of toluene. The solution was concentrated, and left to crystallize at −35° C. 800 mg (28%) of the zirconocene 8 were able to be obtained as the pure racemate in the form of orange-colored crystals.

$^1$H-NMR Spectrum of the racemate (100 MHz, CDCl$_3$): 7.20 (s,2,aromatic-H), 6.97 (s,2,aromatic-H), 6.70 (s,2,β-Ind-H), 2.32 (s,6,CH$_3$), 2.27 (s,6,CH$_3$), 2.20 (s,6,CH$_3$), 1.27 (s,6,Si—CH$_3$).

Mass spectrum: 530 M$^+$ (with respect to $^{90}$Zr), correct isotope pattern, correct disintegration.

Example K

Methylphenylbis ( 2-methyl-4,6-diisopropylindenyl ) silane (9)

18.6 ml (46 mmol) of a 2.5M butyllithium solution in hexane were added to a solution of 10 g (46 mmol) of the indene 4/4a in 200 ml of tetrahydrofuran at room temperature under Ar as an inert gas, and the mixture was heated under reflux for 1 hour. The solution was added dropwise to a solution of 4.48 g (23 mmol) of methylphenyldichlorosilane in 30 ml of tetrahydrofuran at room temperature, and the mixture was heated under reflux for 3 hours. It was poured onto ice-water and extracted several times with ether. The combined organic phases were dried with sodium sulfate and evaporated. The residue was chromatographed on 450 g of silica gel 60. 1.9 g of unreacted indene 4/4a were to be recovered first with a solvent mixture of hexane/methylene chloride (10:1). 7.4 g of the ligand system 9 (isomer mixture) then followed. The yield was 57%, or 73% with respect to the indene reacted.

Example L

Methylphenylsilylbis (2-methyl-4,6-diisopropylindenyl )-zirconium dichloride (10 )

11.2 ml (28 mmol) of a 2.5M butyllithium solution in hexane were added to a solution of 7.4 g (13.5 mmol) of the ligand system 9 in 30 ml of diethyl ether at room temperature under Ar as an inert gas, and the mixture was stirred at room temperature for 16 hours. After the solvent had been stripped off, the residue which remained was dried at 40°–50° C. for 3-4 hours and then added to a suspension of 3.2 g (13.5 mmol) of zirconium tetrachloride chloride in 40 ml of methylene chloride at −78° C. After the mixture had been warmed to room temperature, the solvent was stripped off under reduced pressure. The solid residue which remained was dried under an oil pump vacuum and extracted with 100 ml of hexane. After the solvent had been stripped off, 5.4 g (55%) of the zirconocene 10 were obtained as a mixture of the racemic form with the meso form in a ratio of 2:1 (orange-brown crystalline powder). The pure racemic form is obtainable by recrystallization from hexane.

$^1$H-NMR spectrum of the isomer mixture (100 MHz, CDCl$_3$): 6.6–8.2 (m,aromatic-H,β-Ind-H), 2.5–3.2 (m,i-Pr-H), 2.52 (s,CH$_3$), 2.32 (s,CH$_3$), 2.20 (s,CH$_3$), 1.90 (s, CH$_3$), 1.0–1.5 (m,i—Pr—CH$_3$,Si—CH$_3$).

Mass spectrum: 704 M+ (with respect to $^{90}$Zr), correct isotope pattern, correct disintegration.

Example M 1,2-Bis(2-methyl-4,6-diisopropylindenyl)ethane (11)

18.6 ml (46 mmol) of 2.5M butyllithium solution in hexane were added to a solution of 5.0 g (23.3 mmol) of the indene 4/4a in 50 ml of tetrahydrofuran at room temperature under Ar as an inert gas, and the mixture was heated under reflux for 1 hour. The solution was added to a solution of 2.18 g (11.0 mmol) of 1,2-dibromoethane at −78° C. The solution was warmed slowly to room temperature and stirred overnight at this temperature. The mixture was poured onto ice-water and extracted several times with ether. The combined organic phases were dried with sodium sulfate and evaporated. The residue was chromatographed on 450 g of silica gel 60. 1.2 g of unreacted indene 4/4a were able to be recovered first with a mobile phase mixture of hexane/methylene chloride (20:1 to 10:1). 1.7 g of the ligand system 11 (colorless solid) then followed. The yield was 35%, or 45% with respect to the indene reacted.

Example N 1,2-Ethanediylbis(2-methyl-4,6-diisopropylindenyl)-zirconium dichloride (12)

3.5 ml (8.8 mmol) of a 2.5M butyllithium solution in hexane were added to a solution of 1.6 g (3.52 mmol) of the ligand system 11 in 20 ml of diethyl ether at room temperature under Ar as an inert gas, and the mixture was stirred overnight. The residue which remained after the solvent had been stripped off was washed with hexane and dried under an oil pump vacuum for a long time. The powder thus obtained was added to a suspension of 815 mg (3.5 mmol) of zirconiumtetrachloride in 15 ml of methylene chloride at −78° C. After the mixture had been warmed to room temperature, it was stirred for a further hour, and the solvent was removed under reduced pressure. The residue was dried under an oil pump vacuum and extracted with toluene. After the solvent had been stripped off and the residue had been washed with hexane, 1.5 g (70%) of the zirconocene 18 were obtained as a mixture of the racemic form with the meso form in a ratio of 2:1 (orange-colored powder). 700 mg (32%) of the pure racemate were able to be obtained by recrystallization from a toluene/hexane mixture.

$^1$H-NMR spectrum of the racemate (100 MHz, CDCl$_3$): 7.3 (s,aromatic-H), 7.0 (s,aromatic-H), 6.55 (s,β-Ind-H), 3.6 (s,C$_2$H$_4$), 2.6–3.2 (m,i-Pr-H), 2.2 (s,CH$_3$), 1.0–1.5 (m,i-Pr-CH$_3$)

Mass spectrum: 612 M+ (with respect to $^{90}$Zr), correct isotope pattern, correct disintegration.

Example O 1,2-Bis(2-methyl-4,6-diisopropylindenyl)butane (13)

A solution of 5.0 g (23.3 mmol) of the indene 4/4a was reacted with 2.37 g (11 mmol) of 1,2-dibromobutane (97%) analogously to Example M. Chromatography on silica gel with hexane as the mobile phase gave, after the starting substance and a by-product (spiro compound), 1.16 g (22%) of the ligand 13 as an isomer mixture. The isomers were able to be separated or enriched by another chromatography on a long column.

Example P rac-1,2-Butanediylbis(2-methyl-4,6-diisopropyleneindenyl)zirconium dichloride (14)

A solution of 1.0 g (2.07 mmol) of the ligand system 13 (2 isomers) in 15 ml of diethyl ether was reacted analogously to Example N. Recrystallization from toluene/-hexane mixtures gave, at −35° C., a total of 1.24 g (60%) of the metallocene 14 as a mixture of the various diastereomers of the racemic form and the meso form. The racemate 14 was able to be obtained as 2 diastereomers by another recrystallization.

$^1$H-NMR spectrum (100 MHz, CDCl$_3$): 7.0–7.4 (m,aromatic-H), 6.5 and 6.6 (s, β-Ind-H), 3.3–3.7 (m,C$_2$H$_3$), 1.0–2.8 (m,CH$_3$,i-Pr,C$_2$H$_5$). Mass spectrum: 640 M+, correct isotope pattern, correct disintegration.

POLYMERIZATION EXAMPLES

Example 1

A dry 24 dm$^3$ reactor was flushed with propylene and filled with 12 dm$^3$ of liquid propylene. 35 cm$^3$ of a toluene solution of methylaluminoxane (corresponding to 52 mmol of Al, average degree of oligomerization p=20) were then added and the batch was stirred at 30° C. for 15 minutes.

In parallel thereto, 3.5 mg (0.005 mmol) of racdimethylsilyl(2-methyl-4,6-diisopropyl-1-indenyl)$_2$zirconium dichloride were dissolved in 13.5 cm$^3$ of a toluene solution of methylaluminoxane (20 mmol of Al) and the solution was preactivated by being left to stand for 15 minutes.

The wine-red solution was then introduced into the reactor, the mixture was heated up to 75° C. (10° C./minute) by supplying heat, and the polymerization system was kept at 75° C., by cooling, for 1 hour. The polymerization was stopped by gassing off the excess monomer. 2.11 kg of polypropylene were obtained. The activity of the metallocene was thus 603 kg of polypropylene/g of metallocene×hour.

VN=259 cm$^3$/g, M$_w$=305,000 g/mol; M$_w$/M$_n$=2.0; II=96.0%, MFI (230/5)=8.5 dg/minute.

Comparison Example 1

Example 1 was repeated with the metallocene rac-dimethylsilyl(2-methyl-1-indenyl)$_2$ zirconium dichloride. The metallocene activity was 395 kg of polypropylene/g of metallocene×hour, VN=159 cm$^3$/g, M$_w$=158,000 g/mol, M$_w$/M$_n$=2.1 and the MFI (230/5) was 48 dg/minute. The isotactic index (II) was 96.0%.

Comparison Example 2

Example 1 was repeated with the metallocene rac-dimethylsilyl(2-methyl-4-isopropyl-1-indenyl)$_2$ zirconium dichloride. The metallocene activity was 460 kg of polypropylene/g of metallocene×hour, VN=152 cm³/g, $M_w$=147,500 g/mol, $M_w/M_n$=2.3 and the MFI (230/5) was 51 dg/-minute.

Comparison Example 3

Example 1 was repeated with the metallocene rac-dimethylsilyl(1-indenyl)₂ zirconium dichloride. The metallocene activity was 695 kg of polypropylene/g of metallocene×hour, VN=31 cm³/g, $M_w$=18,500 g/mol, $M_w/M_n$ =2.2 and the MFI (230/5) was no longer measurable.

Comparison Example 4

Example 1 was repeated with the metallocene rac-dimethyl-silyl(4,7-dimethyl-1-indenyl)₂ zirconium dichloride. The metallocene activity was 195 kg of polypropylene/g of metallocene×hour, VN=16 cm³/g, $M_w$=9,500 g/mol, $M_w/M_n$=2.0, II=87%, the MFI (230/5) was no longer measurable.

The four comparison experiments show that polypropylenes prepared using the metallocenes substituted in various ways on the indenyl ligand and polypropylenes prepared using the unsubstituted metallocene show distinct differences in molecular weight. By incorporating the metallocene according to the invention from Example 1, the range extends from the wax range (Comparison Example 4) to the very high molecular weight polymer according to the invention (Example 1).

These experiments demonstrate the superiority of the metallocenes substituted in the 2,4,6-position.

Comparison Example 5

Example 1 was repeated with the metallocene rac-dimethylsilyl(3-methyl-1-indenyl)₂ zirconium dichloride. A polypropylene having an unacceptable isotactic index and a low molecular weight was obtained.

Example 2

Example 1 was repeated with 5.1 mg (0.008 mmol) of the metallocene rac-dimethylsilyl(2-methyl-4,6-diisopropyl-1-indenyl)₂ zirconium dichloride. The polymerization temperature was 50° C. 0.85 kg of polypropylene, corresponding to a metallocene activity of 166.7 kg of polypropylene/g of metallocene×hour, was obtained. VN=454 cm³/g, $M_w$=498,500 g/mol, $M_w/M_n$=2.2, II=97.1%, MFI (230/5)=1.7 dg/minute.

Example 3

Example 1 was repeated with 4.5 mg (0.007 mmol) of the metallocene rac-dimethylsilyl(2-methyl-4,6-diisopropyl-1-indenyl)₂ zirconium dichloride at a polymerization temperature of 60° C. 1.34 kg of polypropylene, corresponding to a metallocene activity of 298 kg of polypropylene/g of metallocene×hour, were obtained. VN=347 cm³/g, $M_w$=444,500 g/mol, $M_w/M_n$=2.1, II=97.0%, MFI (230/5)=3.2 dg/minute, m.p.=145° C.

Example 4

Example 1 was repeated with 9.6 mg (0.015 mmol) of the metallocene rac-dimethylsilyl(2-methyl-4,6-diisopropyl-1-indenyl)2zirconium dichloride at a polymerization temperature of 30° C. Although this polymerization temperature is not very suitable on a large industrial scale, the experiment demonstrates the molecular weight potential and the high activity of the metallocene. 0.61 kg of polypropylene, corresponding to a metallocene activity of 63.5 kg of polypropylene/g of metallocene×hour, was obtained.

VN=645 cm³/g, $M_w$=867,000 g/mol, $M_w/M_n$=2.1, II=97.7%, MFI (230/5)=0.26 dg/minute.

Example 5

Example 1 was repeated with 3.3 mg (0.006 mmol) of the metallocene rac-dimethylsilyl(2,4,6-trimethyl-1-indenyl)₂ zirconium dichloride. 1.83 kg of polypropylene were obtained. The metallocene activity was thus 555 kg of polypropylene/g of metallocene×hour.

VN=165 cm³/g, $M_w$=186,000 g/mol, $M_w/M_n$=2.0, m.p.=145° C., MFI (230/5)=40 dg/minute.

Example 6

Example 1 was repeated with 4.4 mg (0.006 mmol) of the metallocene rac-phenyl(methyl)silyl(2-methyl-4,6-diisopropyl-1-indenyl)₂ zirconiumdichloride at a polymerization temperature of 70° C. 2.05 kg of polypropylene, corresponding to a metallocene activity of 466 kg of polypropylene/g of metallocene×hour, were obtained.

VN=263 cm³/g, $M_w$=385,500 g/mol, $M_w/M_n$=2.5, m.p.=145° C., MFI (230/5)=8.5 dg/minute.

Example 7

Example 6 was repeated with 7.9 mg (0.011 mmol) of the metallocene at a polymerization temperature of 50° C. The metallocene activity was 156 kg of polypropylene/g of metallocene×hour.

VN=498 cm³/g, $M_w$=586,000 g/mol, $M_w/M_n$=3.0, m.p.=147° C., MFI (230/5)=1.5 dg/minute.

Example 8

Example 6 was repeated with 12.0 mg (0.017 mmol) of the metallocene at a polymerization temperature of 30° C. The metallocene activity was 58.3 kg of polypropylene/g of metallocene×hour.

VN=811 cm³/g, $M_w$=1,020,000 g/mol, $M_w/M_n$=2.3, m.p.=148° C., MFI (230/5)=0.2 dg/minute.

Example 9

Example 7 was repeated with 2.8 mg of the metallocene. Before the polymerization, 24 Ndm³ of hydrogen were metered into the reactor. The metallocene activity was 600 kg of polypropylene/g of metallocene×hour.

VN=30 cm³/g, $M_w$=18,250 g/mol, $M_w/M_n$=2.5, m.p.=144° C.

Example 10

Example 7 was repeated with 3.5 mg of the metallocene and with 60 Ndm³ of hydrogen. The metallocene activity was 650 kg of polypropylene/g of metallocene×hour.

VN=14 cm³/g, $M_w$=6,300 g/mol, $M_w/M_n$=2.2, m.p.=145° C.

Examples 9 and 10 demonstrate the excellent responsiveness of the metallocene to hydrogen for establishing a desired molecular weight. With small amounts of hydrogen, the chain length can be varied within wide limits into the wax range.

Example 11

A dry 150dm³ reactor was flushed with nitrogen and filled at 20° C. with 80 dm³ of a dearomatized gasoline cut having a boiling range of 100°–120° C. The gas space was then flushed free from nitrogen; by forcing in 2 bar of propylene and letting down 5 times.

After addition of 50 l of liquid propylene, 64 cm³ of a toluene solution of methylaluminoxane (corresponding to 100 mmol of Al, molecular weight according to kryoscopic determination 1050 g (mol)) were added and the contents of the reactor were heated up to 50° C. A hydrogen content in the gas space of the reactor of 0.2% was established by metering in hydrogen, and was then later kept constant by subsequent metering in throughout the entire polymerization time (checking on-line by gas chromatography).

15.5 mg of rac-phenyl(methyl)silyl(2-methyl-4,6-diisopropyl-1-indenyl)₂ zirconium dichloride were dissolved in 32 ml of a toluene solution of methylaluminoxane (corresponding to 50 mmol of Al) and, after 15 minutes, the solution was introduced into the reactor.

The reactor was kept at a polymerization temperature of 50° C. for 18 hours, by cooling, the polymerization was then stopped by addition of 2 bar of $CO_2$ gas, and the polymer formed was separated off from the suspension medium on a pressure suction filter. The product was dried for 24 hours at 80° C./200 mbar. 20.9 kg of polymer powder, corresponding to a metallocene activity of 74.9 kg of polypropylene/g of metallocene×hour, were obtained.

VN=424 cm³/g, $M_w$=518,000 g/mol, $M_w/M_n$=2.0, m.p.=149° C., MFI (230/5)=4.1 dg/minute.

Example 12

A dry 24 dm³ reactor was flushed with propylene and filled with 2.4 Ndm³ of hydrogen and 12 dm³ of liquid propylene. 35 cm³ of a toluene solution of methylaluminoxane (corresponding to 52 mmol of Al, average degree of oligomerization p=20) were then added. In parallel thereto, 6.5 mg of rac-phenyl(methyl)silyl(2-methyl-4,6-diisopropyl-1-indenyl)zirconium dichloride were dissolved in 13.5 cm³ of a toluene solution of methylaluminoxane (20 mmol of Al), and the solution was preactivated by being left to stand for 5 minutes. The solution was then introduced into the reactor, and the polymerization was carried out at 60° C. for 1 hour, with continuous addition of 60 g of ethylene. The metallocene activity was 398 kg of polypropylene/g of metallocene×hour. The ethylene content of the copolymer was 2.0%.

VN=503 cm³/g, $M_w$=384,000 g/mol, $M_w/M_n$=2.0, m.p.=139° C., according to NMR spectroscopy the ethylene was incorporated predominantly in isolated form (random copolymer).

Example 13

A dry 150 dm³ reactor was filled as in Example 11. 18.9 mg of rac-phenyl(methyl)silyl(2-methyl-4,6-diisopropyl-1-indenyl)₂ zirconium dichloride were dissolved in 32 ml of a toluene solution of methylaluminoxane (50 mmol), and the solution was introduced into the reactor.

The polymerization was carried out at 70° C. for 5 hours in a first stage. In a second stage, 3 kg of ethylene were then rapidly added at 55° C., and after polymerization at 55° C. for a further 3 hours, the reaction was stopped with $CO_2$ gas. 25.9 kg of block copolymer powder were obtained.

VN=344 cm³/g, $M_w$=399,000 g/mol, $M_w/M_n$=3.8, MFI (230/5)=5.0 dg/minute.

The block copolymer contained 10.8% by weight of ethylene. Fractionation showed a content of 27.5% by weight of ethylene/propylene rubber. The glass transition temperature of the rubber was −51° C.

Example 14

Example 1 was repeated at a polymerization temperature of 70° C. with 4.0 mg of the metallocene rac-1,2-ethanediyl-bis(2-methyl-4,6-diisopropyl-1-idenyl)zirconium dichloride. The metallocene activity was 529 kg of polypropylene/g of metallocene×hour.

VN=149 cm³/g, $M_w$=174,500 g/mol, $M_w/M_n$=1.9, m.p.=141° C., MFI (230/5)=74 dg/minute.

Example 15

Example 14 was repeated with 4.0 mg of the metallocene rac-butanediylbis(2-methyl-4,6-diisopropyl-1-indenyl)-zirconiumdichloride. The metallocene activity was 319 kg of polypropylene/g of metallocene×hour.

VN=295 cm³/g, $M_w$=368,500 g/mol, $M_w/M_n$=2.1, m.p.=142° C., MFI (230/5)=4.0 dg/minute.

What is claimed is:

1. A process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$, with the atoms joining them, can form a ring, at a temperature of from −60° to 200° C., under a pressure of 0.5 to 100 bar, in solution, in suspension or in the gas phase, in the presence of a catalyst which is formed from a metallocene as the transition metal compound and a cocatalyst, which comprises using as the metallocene a compound of the formula I

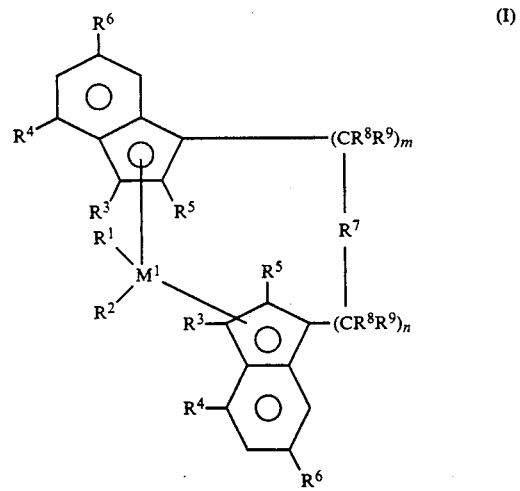

in which
$M^1$ is a metal of group IVb of the periodic table,
$R^1$ and $R^2$ are identical or different and are a hydrogen atom, a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$-alkenyl group, a $C_7$-$C_{40}$-arylalkyl group, a $C_7$-$C_{40}$-alkylaryl group, a $C_8$-$C_{40}$-arylalkenyl group or a halogen atom,
the radicals $R^3$ are identical or different and are a hydrogen atom, a halogen atom, a $C_1$-$C_{10}$-alkyl group, which can be halogenated, a $C_6$-$C_{10}$-aryl group, which can be halogenated, or a —$NR_2^{10}$, —$SR^{10}$, —$OSiR_3^{10}$, —$SiR_3^{10}$ or —$PR_2^{10}$ radical, in which $R^{10}$ is a halogen atom, a $C_1$-$C_{10}$-alkyl group or a $C_6$-$C_{10}$-aryl group, $R^4$ to $R^6$ are identical or different and have the meaning given for $R^3$, with the proviso that $R^4$ and $R^6$ are not hydrogen, $R^7$ is

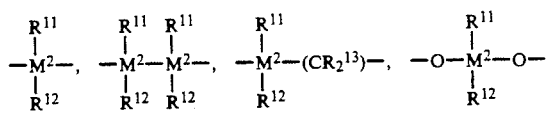

$=BR^{11}$, $=AlR^{11}$, $-Ge-$, $-Sn-$, $-O-$, $-S-$, $=SO$, $=SO_2$, $=NR^{11}$, $=CO$, $=PR^{11}$ or $=P(O)R^{11}$ in which $R^{11}$, $R^{12}$ and $R^{13}$ are identical or different and are a hydrogen atom, a halogen atom, a $C_1-C_{10}$-alkyl group, a $C_1-C_{10}$-fluoroalkyl group, a $C_6-C_{10}$-aryl group, a $C_6-C_{10}$-fluoroaryl group, a $C_1-C_{10}$-alkoxy group, a $C_2-C_{10}$-alkenyl group, a $C_7-C_{40}$-arylalkyl group, a $C_8-C_{40}$-arylalkenyl group or a $C_7-C_{40}$-alkylaryl group, or $R^{11}$ and $R^{12}$, or $R^{11}$ and $R^{13}$, in each case with the atoms joining them, form a ring, $M^2$ is silicon, germanium or tin, $R^8$ and $R^9$ are identical or different and have the meaning given for $R^{11}$ and m and n are identical or different and are zero, 1 or 2, m plus n being zero, 1 or 2.

2. A process as claimed in claim 1, wherein, in formula I, $R^3$ is hydrogen.

3. The process as claimed in claim 1, wherein, in formula I, $M^1$ is Zr or Hf, $R^1$ and $R^2$ are identical or different and are methyl or chlorine, $R^4$ and $R^6$ are identical or different and are methyl, isopropyl, phenyl, ethyl or trifluoromethyl, $R^5$ is hydrogen or has the meanings given for $R^4$ and $R^6$, $R^7$ is a radical

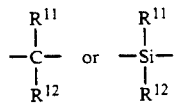

and m plus n is zero or 1.

4. The process as claimed in claim 1, wherein rac-dimethylsilyl(2-methyl-4,6-diisopropyl-1-indenyl)$_2$ zirconium dichloride is used the metallocene of the formula I.

5. The process as claimed in claim 1, wherein an aluminoxane of the formula (II)

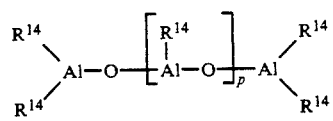

for the linear type, and/or of the formula (III)

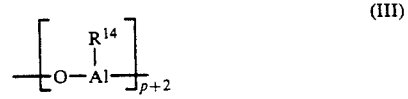

for the cyclic type, in which, in the formulae (II) and (III), the radicals $R^{14}$ are identical or different and are a $C_1-C_6$-alkyl group, a $C_6-C_{18}$-aryl group, benzyl or hydrogen and p is an integer from 2 to 50, is used as the cocatalyst.

6. The process as claimed in claim 1, wherein methylaluminoxane is used as the cocatalyst.

7. The process as claimed in claim 5, wherein, before use in the polymerization reaction, the metallocene of the formula I is preactivated with an aluminoxane of the formula II and/or III.

* * * * *